(12) United States Patent
Thyagarajan et al.

(10) Patent No.: US 12,743,059 B2
(45) Date of Patent: Sep. 22, 2026

(54) SYSTEM AND METHOD FOR FEEDBACK-BASED BEVERAGE SUPERCOOLING

(71) Applicant: Genesee Valley Innovations, LLC, Santa Clara, CA (US)

(72) Inventors: Krishnan Thyagarajan, Sunnyvale, CA (US); Christopher Somogyi, Wimberley, TX (US)

(73) Assignee: Genesee Valley Innovations, LLC, Santa Clara, CA (US)

(*) Notice: Subject to any disclaimer, the term of this patent is extended or adjusted under 35 U.S.C. 154(b) by 746 days.

(21) Appl. No.: 17/876,049

(22) Filed: Jul. 28, 2022

(65) Prior Publication Data

US 2024/0036528 A1 Feb. 1, 2024

(51) Int. Cl.

*G05B 13/02* (2006.01)
*F25D 31/00* (2006.01)
*G01N 33/14* (2006.01)

(52) U.S. Cl.

CPC ......... *G05B 13/024* (2013.01); *F25D 31/005* (2013.01); *G01N 33/14* (2013.01); *A23V 2002/00* (2013.01); *A23V 2300/00* (2013.01)

(58) Field of Classification Search

None

See application file for complete search history.

(56) References Cited

U.S. PATENT DOCUMENTS 2,438,582 A 3/1948 Southerwick
7,237,400 B2 7/2007 Owada
8,464,544 B2 * 6/2013 Shin ........................ F25D 11/02 62/157
10,588,336 B2 3/2020 Jun et al.
2002/0005043 A1 * 1/2002 Rudick ................. F25D 31/007 62/6
2007/0163275 A1 * 7/2007 Ha .......................... F25D 29/00 62/340
2007/0163289 A1 * 7/2007 Hahm .................. F25D 31/007 62/414
2007/0196543 A1 8/2007 Lee et al.
2008/0053124 A1 3/2008 Cho et al.
2008/0245079 A1 * 10/2008 Lim ........................ F25D 23/12 62/426
2008/0245081 A1 * 10/2008 Shin ........................ F25D 23/12 700/275
2011/0165553 A1 7/2011 Elliott et al.
2015/0118369 A1 4/2015 Hyde et al.
2015/0233631 A1 8/2015 Shuntich (Continued)

FOREIGN PATENT DOCUMENTS

CN 108865881 11/2018
CN 110462314 11/2019

(Continued)

*Primary Examiner* — Jenna M Maroney

(74) *Attorney, Agent, or Firm* — Krista A. Wittman

(57) ABSTRACT

A system and method for feedback-based beverage supercooling is provided. An object is identified as a liquid beverage. Cooling is applied to the beverage. The beverage reaches a temperature in a range of −1° C. and −20° C. and maintains a liquid form. The beverage maintains a liquid form via at least one field applied to the beverage. The field is adjusted based on a change in characteristics of the beverage to maintain the liquid form.

14 Claims, 3 Drawing Sheets

(56) References Cited

U.S. PATENT DOCUMENTS

| | | | | |
|---|---|---|---|---|
| 2015/0264968 | A1* | 9/2015 | Shuntich | A23L 5/32 99/275 |
| 2016/0302457 | A1 | 10/2016 | Jun et al. | |
| 2017/0181455 | A1 | 6/2017 | Bullo et al. | |
| 2018/0045458 | A1* | 2/2018 | Shuntich | F25D 3/08 |
| 2018/0149422 | A1* | 5/2018 | Spivey | F25D 31/007 |
| 2018/0180353 | A1* | 6/2018 | Shuntich | F25D 31/007 |
| 2019/0126203 | A1* | 5/2019 | Biegelsen | G01N 15/0656 |
| 2020/0056819 | A1 | 2/2020 | Inada et al. | |
| 2020/0312078 | A1* | 10/2020 | Deshpande | G07F 7/0609 |
| 2020/0323246 | A1 | 10/2020 | Jacobs et al. | |
| 2021/0131718 | A1 | 5/2021 | Jeong et al. | |
| 2021/0161182 | A1 | 6/2021 | Stoenescu et al. | |
| 2021/0403854 | A1 | 12/2021 | Koren et al. | |
| 2022/0003493 | A1 | 1/2022 | Park et al. | |
| 2022/0118136 | A1 | 4/2022 | Church et al. | |
| 2022/0211278 | A1 | 7/2022 | Dede et al. | |
| 2024/0033701 | A1* | 2/2024 | Thyagarajan | A01N 1/144 |
| 2024/0035015 | A1* | 2/2024 | Thyagarajan | C12M 35/02 |
| 2024/0035725 | A1* | 2/2024 | Thyagarajan | F25B 21/00 |
| 2024/0036528 | A1* | 2/2024 | Thyagarajan | G05B 13/024 |

FOREIGN PATENT DOCUMENTS

| | | | | | |
|---|---|---|---|---|---|
| CN | 110906627 | | | 3/2020 | |
| CN | 110953797 | | | 4/2020 | |
| CN | 214593076 | | | 11/2021 | |
| EP | 0765606 | | | 4/1997 | |
| EP | 0584127 | | | 12/1997 | |
| EP | 1980809 | | | 10/2008 | |
| EP | 2499924 | | | 9/2012 | |
| GB | 2476834 | A | * | 7/2011 | F25D 31/007 |
| JP | 2005291525 | | | 10/2005 | |
| JP | 2009030961 | A | * | 2/2009 | F25D 31/007 |
| KR | 20080003136 | | | 1/2008 | |
| KR | 20080088943 | A | * | 10/2008 | |
| KR | 20180054120 | | | 5/2018 | |
| KR | 20220043324 | | | 4/2022 | |
| WO | 2006100740 | | | 9/2006 | |
| WO | 2008004761 | | | 1/2008 | |
| WO | 2008004765 | | | 1/2008 | |
| WO | 2008150104 | | | 12/2008 | |
| WO | 2008153285 | | | 12/2008 | |
| WO | 2015089112 | | | 6/2015 | |
| WO | 2018187840 | | | 10/2018 | |
| WO | 2020023747 | | | 1/2020 | |
| WO | WO-2020138148 | A1 | * | 7/2020 | |
| WO | 20210146122 | | | 7/2021 | |

* cited by examiner 10
11
12
Internetwork
13
14
Server
Identifier
Adjuster
15
Database
Composition
Values
16
17
18
19
20
21
22
23
24
25
26
27

SYSTEM AND METHOD FOR FEEDBACK-BASED BEVERAGE SUPERCOOLING

FIELD

This application relates in general to temperature control and in particular, to a system and method for feedback-based beverage supercooling.

BACKGROUND

A cool beverage is extremely refreshing, especially on a hot day or after exercising. A cold temperatures, beverages maintain taste and extend shelf-life. However, ensuring coldness of the beverage can be difficult due to high temperatures or long lengths of time outside a refrigerator or freezer. For example, previously cooled or frozen beverages that are served in a warm environment or that are generally consumed over a period of time usually become warm and unpalatable prior finishing the beverage. The colder the beverage prior to serving, the longer the beverage remains cold.

However, at a certain point, beverages, even alcohol or carbonated beverages, will freeze, which can be undesirable and cause composition changes of the beverage, and the beverage must then be thawed to liquid form prior to consumption. Specifically, all liquids have a freezing point below which it becomes difficult to maintain the liquid in its intended form and the liquid eventually turns to a solid phase and becomes unavailable for consumption.

Insulated beverage containers, such as made from stainless steel, are extremely popular and function to keep a beverage cool for longer periods of time than traditional plastic or glass containers. Unfortunately, such containers are expensive and bulky, and thus, not feasible for use in restaurants and bars. Dry ice and ice cubes can also be used to keep a beverage cool for longer periods of time. However, ice cubes can dilute the beverage upon melting, and dry ice can cause a physical change in the beverage, including bubbling, as well as generate smoke, which can be undesirable for consumption.

Supercooling is a technique that can be used to cool objects to extremely low temperatures for preservation, such as described in U.S. Pat. No. 10,588,336, to Jun. Supercooling utilizes fields, such as magnetic and electromagnetic fields, to help preserve the physical, nutritional, and sensory characteristics of an object, such as a biological item, while subjecting the object to a temperature below the freezing point of water without freezing the object itself. This is enabled by the suppression or prevention of phase change of both intracellular and intercellular water in the intended object. The fields can include a pulsed/oscillating electric field, pulsed/oscillating magnetic field, or a combination of fields to reorient and induce vibration of water molecules in the object (among other physico-chemical controls), thus suppressing or preventing the formation of ice from the water molecules.

While applicable to many kinds of objects, supercooling is of a particular interest in preserving biological items, such as food, organs, produce, tissues, stem cells, embryos, vaccines, water-based medicines, and blood, with achieving and maintaining a supercooled state of the biological item being possible due to oscillating/pulsed magnetic fields or oscillating/pulsed electric fields or a combination thereof, which prevents nucleation or freezing of the water contained in the biological item.

However, conventional techniques for supercooling do not account for differences in the biological items' characteristics and do not allow for a near-real-time assessment of the status of the supercooled object to provide a closed-loop feedback, thus complicating achieving a desired result. In particular, achieving a state of supercooling requires an approach tailored to individual characteristics of the objects being supercooled. For instance, based on the composition of a specific object, different field characteristics such as field strength, frequency, phase, and waveform, are necessary for different types of objects. Determining the correct characteristics and their values in order to achieve supercooling and prevent ice-nucleation can be difficult to determine due to many factors, including size, shape, and content of the object, and many of the general public may experience difficulty in maintaining supercooling conditions based on a lack of knowledge of object composition and lack of monitoring capabilities. In addition, the fields that were appropriate previously, may no longer be suitable for continuing the supercooling process.

With respect to beverages, there are many different types and profiles of beverages, including water, fruit-based, carbonated beverages, and alcohol, such as beer, vodka, wine, gin, tonic, absinth, rum, and whisky. Each different type of beverage has different characteristics that make a single approach to supercooling unsuccessful. For instance, beverages with higher alcohol content have a lower freezing temperature than non-alcoholic beverages or beverages with lower alcohol content.

Accordingly, a feedback process for supercooling beverages, including carbonated beverages and alcohol, without initiating freezing is needed. Preferably, the field applied to achieve supercooling is tailored based on characteristics of the object being supercooled, as the ability to change the supercooling characteristics on the fly is important to obtain optimum energy-efficient supercooling. At cooler temperatures, a beverage can remain cooler for longer periods of time and certain flavor profiles can be added to the beverage that previously could not be added at higher temperatures.

SUMMARY

A feedback process that identifies characteristics of an object and utilizes the characteristics to initiate and adjust a field applied to the object is provided. In one embodiment, the process leverages machine learning to automatically identify a condition of the object and adjust the supercooling parameters. Sensors are utilized during supercooling to monitor a condition of the object being supercooled. Specifically, characteristics of the object are measured at different points, areas, or volumes on the object and the measurements are used to determine whether supercooling is being achieved or whether the object is starting to freeze. Based on the measurements, parameters of the field can be adjusted to ensure supercooling of the object without undergoing a phase change, including changing from a liquid to a solid. Additionally, by utilizing a feedback system of supercooling, a beverage can reach temperatures below 0° C. or below the freezing point of that particular beverage without the incorporation of any chemical additives, while minimizing the effect on the quality of the intended experience, including fizziness, taste, texture, color, and smell.

An embodiment provides a system and method for feedback-based beverage supercooling is provided. An object is identified as a liquid beverage. Cooling is applied to the beverage. The beverage reaches a temperature in a range of −1° C. and −20° C. and maintains a liquid form. The beverage maintains a liquid form via at least one field applied to the beverage. The field is adjusted based on a change in characteristics of the beverage to maintain the liquid form.

Still other embodiments of the present invention will become readily apparent to those skilled in the art from the following detailed description, wherein is described embodiments of the invention by way of illustrating the best mode contemplated for carrying out the invention. As will be realized, the invention is capable of other and different embodiments and its several details are capable of modifications in various obvious respects, all without departing from the spirit and the scope of the present invention. Accordingly, the drawings and detailed description are to be regarded as illustrative in nature and not as restrictive.

DETAILED DESCRIPTION

Supercooling can be applied to food and other water-containing objects, such as organic matter and biological items. During supercooling, the water-containing objects are preserved by cooling the objects to a temperature below the freezing point of water or the freezing point of the liquid to undergo supercooling without initiating the formation of ice within or on the object. Further, supercooling minimizes any effect on the quality of experiencing a particular beverage, including fizziness, taste, texture, color, and smell without introducing any chemical additives. However, ensuring that the water in the object does not freeze, by turning to ice, can be difficult and the object should be monitored closely. A feedback system can monitor characteristics or conditions of an object under supercooling conditions, determine new parameters for the supercooling fields applied, and make adjustments to the fields based on the new parameters. Specifically, the beverage can be exposed to low doses of electromagnetic or acoustic energy pulses that are adjusted over time to prevent phase-change of water-based components of the liquid beverage from a liquid to a solid.

Figure 1:
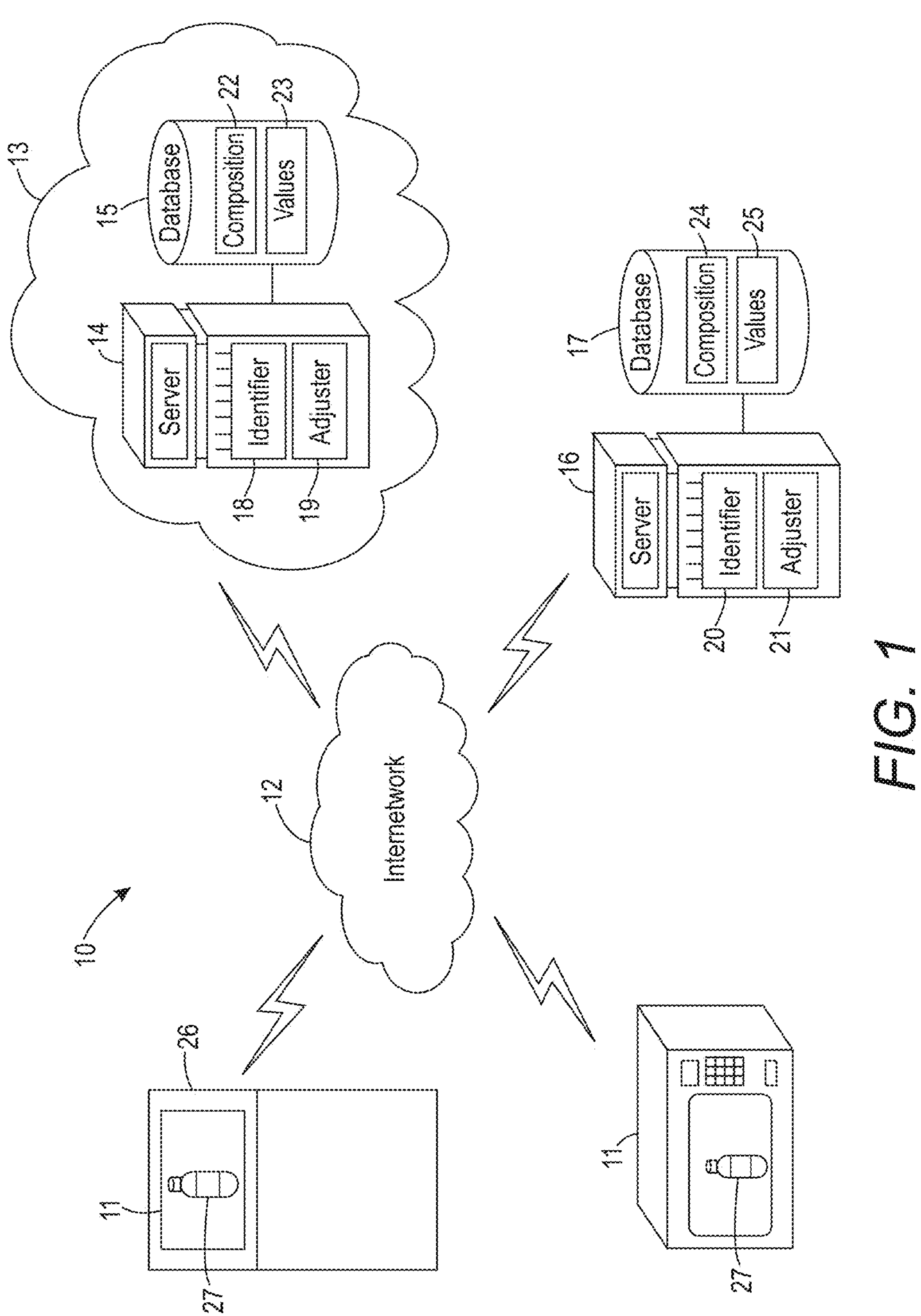
FIG. 1 is a block diagram showing a system for feedback-based beverage supercooling in accordance with one embodiment.

Utilizing a feedback system during supercooling helps prevent phase change of an object to a solid, including nucleation of water in a beverage, in a much more optimum manner. FIG. 1 is a block diagram showing a system 10 for feedback-based beverage supercooling in accordance with one embodiment. A supercooling device 11 can supercool an object, such as a beverage 27, to a temperature below the freezing point of water without freezing the beverage by applying one or more fields to the beverage, including magnetic, electric, and electromagnetic fields. The supercooling device 11 can be a standalone device or the components of the supercooling device can be incorporated into an appliance, such as a refrigerator or another freezer 26, and is described in detail below with respect to FIG. 3. In a further embodiment, components of the supercooling device 11 can be included in a housing and together, inserted into an appliance.

When incorporated into another appliance that has a cooling function, the supercooling device utilizes that cooling function to lower the temperature of the water. However, when used as a standalone device, the supercooling device can include a cooling system to lower the temperature of the water to a range of −1° C. to −30° C. In a further embodiment, components of the supercooling device 11 can be included in a housing and together, inserted into an appliance.

The supercooling device 11 communicates with a feedback server 14, 16 via an internetwork 12, such as the Internet or cellular network, to obtain and adjust parameters of the field based on the obtained characteristics. In one embodiment, the feedback server 14 can be a cloud-based server. Alternatively, the server 16 can be locally or remotely located with respect to the supercooling device 11. The feedback server 14, 16 can include an identifier 18, 20 and an adjuster 19, 21. The identifier 18, 20 can utilize measurements for characteristics of the beverage obtained from the supercooling device 11 to determine an identity or classification of the beverage based on known composition values 22, 24 of beverages stored in a database 15, 17 associated with the server 14, 16. For example, the beverage can be identified as a beverage. Additionally, the beverage can be further classified as juice, water, soda, alcohol, or another type of beverage. Machine learning can also be used in lieu of or in addition to a look up table of compositions and identities or classifications. In a further embodiment, identification or classification of a beverage can occur on the supercooling device 11, such as via a processor, which is described in detail below with respect to FIG. 3.

The adjuster 19, 21 utilizes data obtained from the supercooling device 11 regarding the beverage and the field to determine whether the field should be adjusted to ensure an appropriate supercooling temperature is reached, without allowing nucleation of ice via the water content in the beverage. The adjustment can be determined using characteristic values 23, 25 for the beverage and parameter values for the field, which are stored by the databases 15, 17 to determine new parameter values for the field. In a further embodiment, ranges of beverage characteristics and field parameters can be stored on the supercooling device 11 for use in adjusting the supercooling fields applied to a beverage. Alternatively, machine learning can also be used to determine and adjust field parameters in lieu of a stored look up table of characteristic values and parameters.

Figure 2:
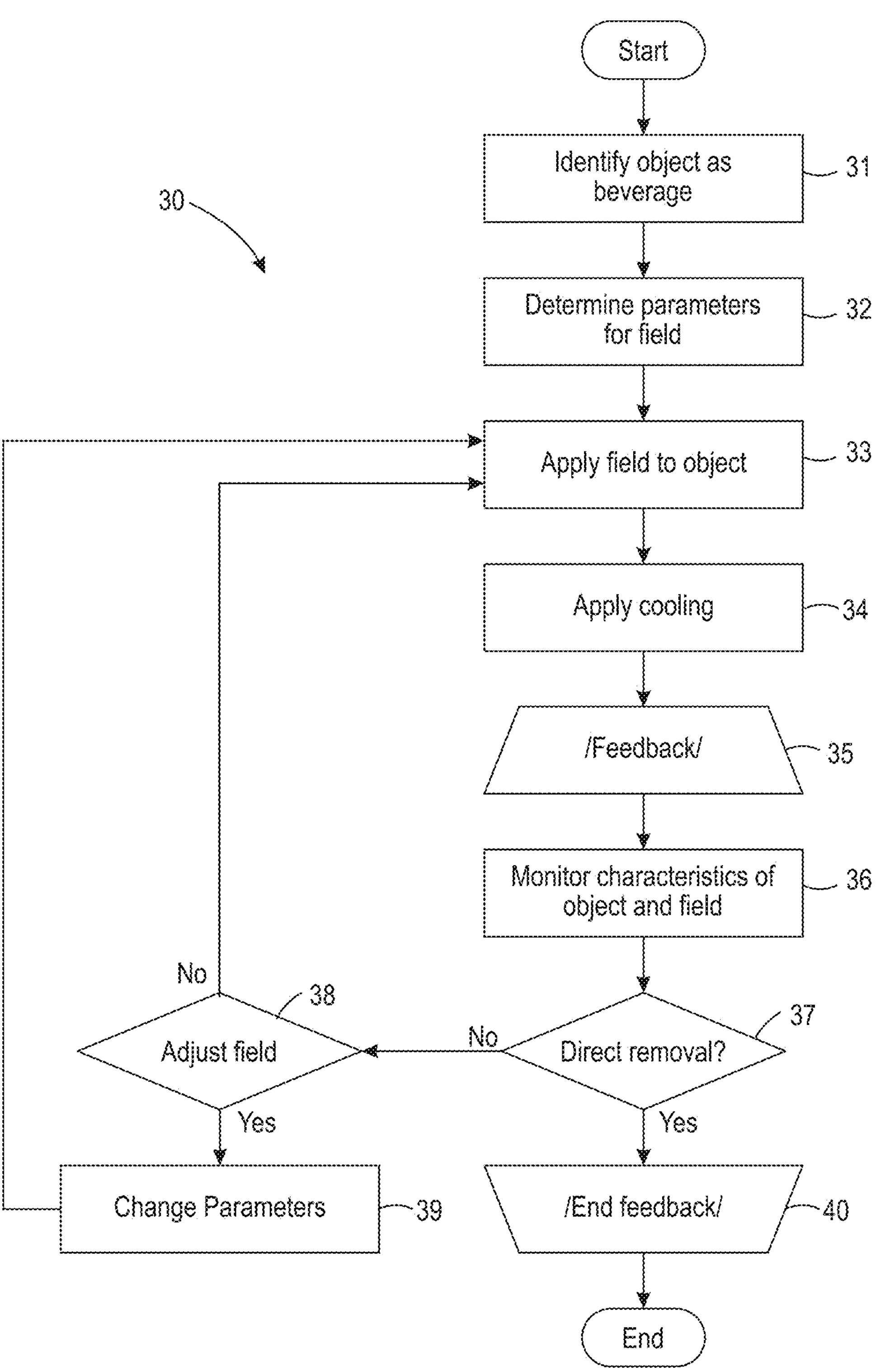
FIG. 2 is a flow diagram showing a method for feedback-based beverage supercooling in accordance with one embodiment.

The ability to automatically determine a composition of a beverage, and determine and adjust parameters for supercooling helps to maintain supercooling conditions of the beverage, while preventing ice-nucleation and freezing of the beverage. FIG. 2 is a flow diagram showing a method 30 for feedback-based supercooling in accordance with one embodiment. A beverage to be supercooled is placed into a supercooling device and can be identified (step 31) as a beverage based on input from a user or via sensors of the device. The beverage can include water, juice, juice-based or water-based beverages, carbonated or aerated beverages, such as soda or seltzer, and alcohol, as well as many other types of drinks. When introduced to the device for supercooling, the beverage can be contained in a beverage container, such as a glass or plastic bottle, tin can, juice box, pan, large bins or other type of container as a single serving or in bulk.

When provided by the user, the type of beverage or name of the beverage can be entered into the supercooling device or computer application associated with the supercooling device. When sensors are utilized, one or more sensors can send signals towards the beverage, and information about the beverage is obtained via the signal, which is returned back to the sensor. Passive and active sensors can be used, including imaging and reflective sensors, as well as electro-current sensors, optical sensors, chemical sensors, electrochemical sensors, acoustic sensors, ultrasound sensors, and hyperspectral imaging.

Measures for characteristics, such as a density of the beverage, alcohol content, water content or air versus water content, amount of pressure in a container of the beverage, movement of bubbles in the beverage, and dissolved particulate matter in the beverage, as well as other characteristics, can be obtained via the sensors. For example, hyperspectral imaging can be used to determine a fizziness, gas content, or chemical composition of the beverage object. The identified characteristics can be used to classify the beverage as a beverage or a type of beverage, instead of a food, biological, or other type of beverage. The identity or classification of the beverage can then be determined via a look up table, which includes characteristics, values for the characteristics, and identities or categories for the beverage, based on the identified characteristics and measures.

Additionally or in lieu of the identified characteristics, identification of the beverage can occur via a camera or determined via machine learning. When used, a camera can obtain an image of the beverage that can be compared with a database of images to determine an identity of the beverage. For example, a small paper box can indicate juice as the beverage, while a larger paper box and a presence of alcohol may indicate wine. With respect to machine learning, the characteristics can be input and an identification or classification of the beverage is output. Data used for training can include different types of objects each associated with different combinations of characteristics and characteristic values, as well as specific types of beverages each associated the different combinations of characteristics and characteristic values.

Initial parameters for a field applied during supercooling can be determined (step 32) based on the characteristics of the beverage, or the identity or classification of the beverage, if known. Specifically, when an identity of the beverage is not known, one or more of the characteristics can be used to determine a type of field and initial parameters for the determined field. In one example, beverages with higher alcohol content freeze at lower temperatures than beverages without alcohol and thus, the initial parameters can reflect such characteristic. Further, the type of field to be applied can be based on the type of container in which the beverage is housed. For example, when a magnet is used, non-magnetic containers such as glass are preferred to prevent noise or inaccurate readings of beverage characteristics based on a presence of the container. The field to be applied can include one or more of a magnetic field, electric field, an electromagnetic field, or a combination of fields. Other types of fields are possible.

Meanwhile, the field parameters can include amplitude, frequency, phase, waveform, and duration, as well as other types of parameters. Values for the parameters can be determined using a look up table, which can provide field parameter values for objects, such as beverages, food or biological objects, based on a characteristic or a combination of characteristics, or based on an identity or classification of the object. In a further embodiment, machine learning can be used to determine the initial field parameters. The learning can be performed based on data sets of the characteristic values and parameters for fields to be applied to each different object. Once the parameters are determined, the field is then applied (step 33) to the beverage based on the values of the parameters.

Prior to, concurrently with, or subsequently, cooling is applied (step 34) to the beverage. The cooling can be produced by a compressor in a cooling system, such as a refrigeration or freezer system that can also include a condenser and evaporator. In one example, traditional refrigeration or freezer systems can be used. Other types of cooling systems can also be used. At a minimum, the cooling system should be able to cool the beverage to a temperature between −1° C. to −20° C.

To maintain supercooling conditions, such that the beverage does not begin to nucleate below freezing temperatures, a feedback system is run (step 35). In one embodiment, desirable supercooling conditions can include a temperature range of about −1° C. to −20° C. While undergoing supercooling, the beverage can be monitored (step 36) continuously or at predetermined time periods to determine a condition of the beverage based on characteristics of the beverage. Also, the beverage can be monitored at different spatial points at different times or at the same time. The characteristics can be measured through the container in which the beverage is housed. For instance, a hyperspectral sensor can normalize signals obtained through glass containers versus tin containers and can calibrate for the differences between the signals of the different containers.

The characteristics monitored can include temperature, water content or air versus water content, amount of pressure in a container of the beverage, movement of bubbles in the beverage, and dissolved particulate matter in the beverage, as well as other characteristics, can be obtained via the sensors. For example, an acoustic sensor can determine a measure of movement of bubbles, if any, in the beverage. In addition to or alternatively, an ultrasound sensor can measure bubbles.

Also, given a measure of pressure inside the container, an average motion of any bubbles present can be determined. If the average motion of the bubbles or pressure changes, a change to the beverage is occurring and may indicate initiation of nucleation of the beverage. Bubble size and type can also be helpful in determining an identity of the beverage. During carbonation, carbon dioxide or nitrogen can be used. Nitrogen bubbles are typically smaller that bubbles formed via carbon dioxide and a presence, along with other characteristics, can indicate a type of beverage. For example, most beers use carbon dioxide for carbonation; however, Guinness beer uses nitrogen-based carbonation. Further, an amount of the carbon dioxide or nitrogen can be used to help identify the beverage since beverages include different volumes of gas for carbonation.

Parameters of the applied field can also be monitored (step 36), including wavelength, frequency, phase, amplitude, waveforms, and duration. If at any time during cooling (step 34) and monitoring (step 36) of the beverage, removal of the beverage is detected (step 37), then cooling and monitoring of the beverage ends and the feedback system and supercooling process is completed for that beverage (step 40). The beverage can be removed via continuous dispensation, similar to a soda fountain or draft beer dispenser, where the beverage can be dispensed from the container on demand. Alternatively, the beverage can be prebottled or packaged and removed to provide to a user for consumption.

However, if the beverage remains in the supercooling device under supercooling conditions, the monitored characteristics of the beverage and parameters of the field can be used to determine whether the field needs to be adjusted (step 38). If the beverage is determined to be under appropriate supercooling conditions, such that the beverage reaches a temperature between −1° C. and −20° C., no nucleation of the water molecules in the beverage has commenced and water molecules in the beverage are still mobile, then no adjustments may be necessary and the field is continued (step 33). If nucleation or freezing is beginning, the density of the beverage can change as the water in the air pockets freeze and expansion occurs. The propagation of sound through ice and water are different as well, thus acoustic sensors can be used to determine the beginning of the formation of ice (if it occurs).

If the beverage appears to be close to or actually undergoing nucleation, adjustments to the field parameters should be made (step 39). The parameter adjustments can include a change in amplitude, frequency, phase, waveform, wavelength, and duration of the field, which can affect mobility, physical movement or ability of phase-change of water molecules in the beverage to prevent or reverse nucleation. The field changes can be made manually or automatically. In one embodiment, different formulas can be used to determine new parameter values based on the monitored characteristics of the beverage, as well as a graph of beverage characteristics and calibration of the fields. The graph can include values for the listed characteristics with standard deviations and known progression of time with temperatures for each beverage with a particular characteristic or combination of characteristics to achieve supercooling. In a different embodiment, machine learning can be used to determine new values for the field parameters.

Returning to the above example, after the beverage is determined to be undergoing nucleation or freezing, the field parameters can be adjusted. New values of the parameters can be determined via machine learning or a graph. For instance, if freezing is occurring, the frequency and wavelength of the field application to the beverage may be increased to result in additional mobility of the water molecules to prevent freezing. After the parameters are changed, the field is applied (step 33) to the beverage using the adjusted parameters and the feedback process continues (step 35). For example, a magnetic field can be changed by moving the magnets closer to or away from the beverage, or moving the magnets relative to one another. Movement of the magnets can be manual or automated.

Figure 3:
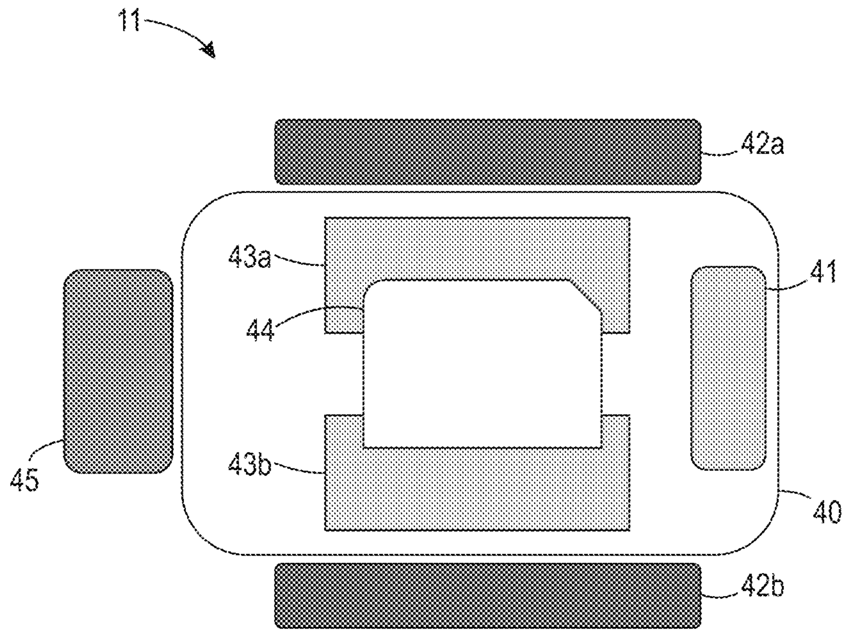
FIG. 3 is a block diagram showing, by way of example, a device for feedback-based beverage supercooling.

The device used to perform feedback-based supercooling can vary in size depending on the beverages to be supercooled. FIG. 3 is a block diagram showing a top view of a device 11 for feedback-based beverage supercooling in accordance with one embodiment. The supercooling device 11 can include a receptacle 40 in which a beverage 44 is placed to undergo supercooling. The receptacle 40 can include a container, pan, or other type of receptacle for holding the beverage 44. In one embodiment, the receptacle 40 is placed into a standalone housing (not shown), similar to a microwave, to initiate supercooling or alternatively, can be incorporated into an appliance, such as a refrigerator.

One or more field generators 42*a,b*, 43*a,b* can be positioned with respect to the receptacle 40. The field generators can each include a magnet, electrode, wires, electromagnets, or other material systems, such as 2D materials, including for example, graphene, van-der-waals layered materials or organic conductive polymers. For example, electrodes 43*a, b* can be positioned on a bottom side of the receptacle, along an interior surface, to generate a pulsed electric field. Other positions of the electrodes are possible, including on opposite sides (not shown) of the receptacle 40. When placed in a position other than the bottom of the receptacle, the electrodes can be affixed to walls of the standalone housing or walls of a housing, such as an appliance. The electrodes can be positioned to contact the beverage or in a further embodiment, can be placed remotely from the beverage.

The supercooling device 11 can also include at least one magnet 42*a, b*, such as an electromagnet, a permanent magnet, or a combination of magnets, to generate an oscillating magnetic, electric or electromagnetic field. Time-varying magnetic fields can be used to create electric fields and vice-versa. The magnets can be positioned along one or more sides of the receptacle 40, or can be affixed to the receptacle itself or the housing in which the receptacle is placed. In a further embodiment, the magnets can be remotely located from the receptacle and the field emitted from the magnets can be applied to the beverage via one or more transducers.

Further, at least one closed-loop monitoring sensor 41 can be provided adjacent to the receptacle on one or more sides. Alternatively or in addition, a sensor can be affixed to the housing, on an interior surface, in which the receptacle is placed for supercooling. The monitoring sensors can include imaging and reflective sensors, electrocurrent sensors, chemical sensors, electric sensors, acoustic sensors, optical sensors, electrochemical sensors, thermal sensors and imagers, and hyperspectral sensors. However, other types of sensors are possible.

An electrical control unit 45 can be a processor that is interfaced to the sensors 41, magnets 42*a,b*, and electrodes 43*a,b* to communicate during the feedback process. Specifically, the processor can determine an identity of or classify an object, such as a beverage, for supercooling based on measurements from the sensors 41, as well as identify parameters for the field to be applied based on the identity or classification. The processor can also instruct the sensors 41 to measure characteristics of the beverage undergoing supercooling and in turn, receive the measured values as feedback for determining if new parameters of the field are needed and if so, values of the parameters. Based on the feedback from the sensors, the processor can communicate the new parameter values with the magnets and electrodes to change the field applied to the beverage for changing the supercooling conditions.

In a further embodiment, the processor can obtain data from the sensors, electrodes, and magnets for providing, via a wireless transceiver included in the device, to a cloud-based server for determining an identity or classification of the beverage, determining initial parameters for the field, and identifying new field parameters for adjusting the field. When performed in the cloud, the data set of beverage identities and classifications, initial parameters, and guidelines for adjusted parameters can be utilized by different users. In contrast, when the processor of the supercooling device performs such actions, the data sets are specific to that supercooling device.

While the description above focuses on beverages, the supercooling device and process can also be applied to different kinds of objects, including raw, preserved or cooked foods, blood, embryos, vaccines, probiotics, medicines, sperm, tissue samples, plant cultivars, cut flowers and other plant materials, biological samples of plants, animal, microbial, and fungal materials, non-biologicals, such as hydrogel materials, material that can be impacted by water absorption, such as textiles, nylons and plastic lenses and optics, fine instruments and mechanical components, heat exchangers, and fuel, as well as ice as described in commonly-assigned U.S. patent application, entitled "System and Method for Controlling Crystallized Forms of Water," Ser. No. 17/875,939, filed Jul. 28, 2022, pending; organic items as described in commonly-assigned U.S. patent application, entitled "System and Method for Feedback-Based Nucleation Control," Ser. No. 17/876,010, filed Jul. 28, 2022, pending and commonly-assigned U.S. patent application, entitled "Feedback-Based Device for Nucleation Control," Ser. No. 17/875,957, filed Jul. 28, 2022, pending, colloids as described in commonly-assigned U.S. patent application, entitled "System and Method for Feedback-Based Colloid Phase Change Control," Ser. No. 17/875,969, filed Jul. 28, 2022, pending; agriculture as described in commonly-assigned U.S. patent application, entitled "System and Method for Controlling Cell Functioning and Motility with the Aid of a Digital Computer," Ser. No. 17/876,065, filed Jul. 28, 2022, pending; lab grown material, including meat, as described in commonly-assigned U.S. patent application, entitled "System and Method for Controlling Cellular Adhesion with the Aid of a Digital Computer," Ser. No. 17/876,072, filed Jul. 28, 2022, pending; and food as described in commonly-assigned U.S. patent application, entitled "System and Method for Metamaterial Array-Based Field-Shaping," Ser. No. 17/875,959, filed Jul. 28, 2022, pending the disclosures of which are incorporated by reference. Further, a receptacle packaging can be used to hold the beverage to prevent liquid of the beverage from touching electrode contacts as described in commonly-assigned U.S. patent application, entitled "Contact Interfacing Material Receptabele," Ser. No. 17/875,991, filed Jul. 28, 2022, pending, the disclosure of which is incorporated by reference.

While the invention has been particularly shown and described as referenced to the embodiments thereof, those skilled in the art will understand that the foregoing and other changes in form and detail may be made therein without departing from the spirit and scope of the invention.

What is claimed is:

1. A method for feedback-based beverage supercooling, comprising:
- identifying an object as a liquid beverage;
- determining an identity or classification of the liquid beverage, comprising:
  - obtaining via sensors, measurements for one or more characteristics of the liquid beverage other than temperature;
  - comparing the obtained values for the one or more characteristics with known composition values for a variety of beverages, wherein the known composition values are stored in a database and obtained prior to identification of the object as a liquid beverage; and
  - assigning an identity or classification of the liquid beverage based on the obtained measurements for the one or more characteristics and the known composition values;
- applying cooling to the beverage based on the assigned identity or classification, wherein the beverage reaches a temperature in a range of −1° C. and −20° C. and maintains a liquid form; and
- maintaining the liquid form of the beverage using at least one field applied to the beverage, wherein the field is adjusted based on a change in the one or more characteristics of the beverage.

2. A method according to claim 1, further comprising:
- applying the field to the beverage via one or more sensors.

3. A method according to claim 1, wherein each sensor comprises one of an imaging sensor, reflective sensor, electrocurrent sensor, optical sensor, chemical sensor, electrochemical sensor, acoustic sensor, ultrasound sensor, and hyperspectral imaging sensor.

4. A method according to claim 1, wherein the characteristics of the liquid beverage comprise one or more of alcohol content, an amount of pressure in a container housing the beverage, alcohol content, air versus water content of the beverage, and an amount of dissolved particular matter.

5. A method according to claim 4, wherein the object is identified as a beverage based on input from a user or based on one or more characteristics of the beverage.

6. A method according to claim 1, further comprising:
- determining parameters for the adjusted field based on the obtained measures.

7. A method for supercooling beverages, comprising:
- identifying an object as a liquid beverage;
- determining an identity or classification of the liquid beverage, comprising:
  - obtaining via sensors, values for one or more characteristics of the liquid beverage other than temperature;
  - comparing the obtained values for the one or more characteristics with known composition values for a variety of beverages, wherein the known composition values are stored in a database and obtained prior to identification of the object as a liquid beverage; and
  - assigning an identity or classification of the liquid beverage based on the obtained values for the one or more characteristics and the known composition values;
- determining parameters for at least one field to be applied to the beverage based on the assigned identity or classification of the liquid beverage;
- supercooling the beverage to a temperature between −1° C. and −20° C. by applying the field to the beverage using the determined parameters;
- measuring the one or more of the characteristics of the beverage or one or more characteristics of the field during the supercooling; and
- adjusting the field based on at least one of the characteristics of the beverage or the field.

8. A method according to claim 7, further comprising:
- determining the identity of the object as the beverage using input from a user the values of the characteristics of the beverage.

9. A method according to claim 7, wherein the characteristics of the beverage comprise one or more of alcohol content, an amount of pressure in a container housing the liquid beverage, alcohol content, air versus water content of the beverage, and an amount of dissolved particular matter.

10. A method according to claim 7, further comprising:
- determining one or more new parameters for the adjusted field based on the characteristics of the beverage or the field.

11. A method according to claim 7, wherein the new parameters are determined via machine learning or a look-up table.

12. A method according to claim 7, further comprising:
- applying the field to the beverage via one or more sensors, each sensor comprising comprises one of an imaging sensor, reflective sensor, electrocurrent sensor, optical sensor, chemical sensor, electrochemical sensor, acoustic sensor, ultrasound sensor, and hyperspectral imaging sensor.

13. A method according to claim 7, wherein the beverage is housed in a container comprising one or more of tin, aluminum, plastic, glass, paper, and cardboard.

14. A method according to claim 7, wherein the beverage comprises one or more of water, fruit juice, vegetable juice, sugar, carbonation, soda, and alcohol.

* * * * *